US010052108B2

(12) United States Patent
Aguilar et al.

(10) Patent No.: US 10,052,108 B2
(45) Date of Patent: Aug. 21, 2018

(54) DEVICES AND METHODS FOR DELIVERING AN IMPLANT TO A VASCULAR DISORDER

(71) Applicant: INCUMEDx, Inc., Fremont, CA (US)

(72) Inventors: Amiel Richard Aguilar, San Jose, CA (US); Crystal Kay Sein-Lwin, Hayward, CA (US); Nga Doan, San Jose, CA (US); Berchell John Yee, Fremont, CA (US)

(73) Assignee: INCUMEDx, Inc., Fremont, CA (US)

( * ) Notice: Subject to any disclaimer, the term of this patent is extended or adjusted under 35 U.S.C. 154(b) by 280 days.

(21) Appl. No.: 14/928,212

(22) Filed: Oct. 30, 2015

(65) Prior Publication Data
US 2017/0119399 A1 May 4, 2017

(51) Int. Cl.
*A61M 29/00* (2006.01)
*A61B 17/12* (2006.01)

(52) U.S. Cl.
CPC .... *A61B 17/1214* (2013.01); *A61B 17/12113* (2013.01); *A61B 2017/12054* (2013.01)

(58) Field of Classification Search
CPC .... A61M 29/00; A61B 17/04; A61B 17/1214; A61B 17/12113; A61B 2017/12054; A61B 17/12
See application file for complete search history.

(56) References Cited

U.S. PATENT DOCUMENTS

| 5,250,071 A | 10/1993 | Palermo |
| 5,261,916 A | 11/1993 | Engelson |
| 5,263,964 A | 11/1993 | Purdy |
| 5,290,230 A | 3/1994 | Ainsworth et al. |

(Continued)

FOREIGN PATENT DOCUMENTS

| EP | 1010396 A1 | 6/2000 |
| EP | 1621149 A1 | 2/2006 |

(Continued)

OTHER PUBLICATIONS

Extended European Search Report for EP dated dated May 22, 2015, 6 pages.

(Continued)

*Primary Examiner* — Victor Nguyen
(74) *Attorney, Agent, or Firm* — Goodwin Procter LLP

(57) ABSTRACT

A device for delivering an implant (e.g., an embolic microcoil) to a vascular disorder of a patient includes a delivery pusher, a moveable element, and first and second elongate members. The delivery pusher defines a lumen between its proximal and distal ends. The moveable element (e.g., a floating tube or a floating coil) defines a passageway therethrough and is disposed within the lumen of the delivery pusher. The first and second elongate members (e.g., core wires) are also disposed within the lumen of the delivery pusher. A portion of each elongate member passes through the passageway of the moveable element. Movement of the first elongate member in a first direction (e.g., retraction of the first elongate member from a locked to an unlocked configuration) causes a time-delayed or lost motion movement of the second elongate member in the same (i.e., first) direction, which releases the implant from the delivery pusher.

23 Claims, 12 Drawing Sheets

(56) References Cited

U.S. PATENT DOCUMENTS

| | | | |
|---|---|---|---|
| 5,304,195 A | 4/1994 | Twyford, Jr. et al. | |
| 5,312,415 A | 5/1994 | Palermo | |
| 5,350,397 A | 9/1994 | Palermo et al. | |
| 5,451,209 A | 9/1995 | Ainsworth et al. | |
| 5,582,619 A | 12/1996 | Ken | |
| 5,690,667 A | 11/1997 | Gia | |
| 5,725,546 A | 3/1998 | Samson | |
| 5,792,154 A | 8/1998 | Doan et al. | |
| 5,797,928 A * | 8/1998 | Kogasaka | A61B 17/0469 606/139 |
| 5,814,062 A | 9/1998 | Sepetka et al. | |
| 5,833,705 A | 11/1998 | Ken et al. | |
| 5,853,418 A | 12/1998 | Ken et al. | |
| 5,868,754 A | 2/1999 | Levine et al. | |
| 5,911,737 A | 6/1999 | Lee et al. | |
| 5,944,733 A | 8/1999 | Engelson | |
| 6,004,338 A | 12/1999 | Ken et al. | |
| 6,013,084 A | 1/2000 | Ken et al. | |
| 6,022,369 A | 2/2000 | Jacobsen et al. | |
| 6,068,644 A | 5/2000 | Lulo et al. | |
| 6,193,728 B1 | 2/2001 | Ken et al. | |
| 6,221,066 B1 | 4/2001 | Ferrera et al. | |
| 6,238,415 B1 | 5/2001 | Sepetka et al. | |
| 6,280,457 B1 | 8/2001 | Wallace et al. | |
| 6,296,622 B1 | 10/2001 | Kurz et al. | |
| 6,478,773 B1 | 11/2002 | Gandhi et al. | |
| 6,551,305 B2 | 4/2003 | Ferrera et al. | |
| 6,562,021 B1 | 5/2003 | Derbin et al. | |
| 6,835,185 B2 | 12/2004 | Ramzipoor et al. | |
| 6,887,235 B2 | 5/2005 | O'Connor et al. | |
| 6,966,892 B2 | 11/2005 | Gandhi et al. | |
| 7,137,990 B2 | 11/2006 | Hebert et al. | |
| 7,166,122 B2 | 1/2007 | Aganon et al. | |
| 7,198,613 B2 | 4/2007 | Gandhi et al. | |
| 7,255,707 B2 | 8/2007 | Ramzipoor et al. | |
| 7,377,932 B2 | 5/2008 | Mitelberg et al. | |
| 7,422,569 B2 | 9/2008 | Wilson et al. | |
| 7,485,122 B2 | 2/2009 | Teoh | |
| 7,608,089 B2 | 10/2009 | Wallace et al. | |
| 7,695,484 B2 | 4/2010 | Wallace et al. | |
| 7,722,636 B2 | 5/2010 | Farnan | |
| 7,901,444 B2 | 3/2011 | Slazas | |
| 7,938,845 B2 | 5/2011 | Aganon et al. | |
| 7,942,894 B2 | 5/2011 | West | |
| 7,972,342 B2 | 7/2011 | Gandhi et al. | |
| 7,985,238 B2 | 7/2011 | Balgobin et al. | |
| 8,062,325 B2 | 11/2011 | Mitelberg et al. | |
| 8,328,860 B2 | 12/2012 | Strauss et al. | |
| 8,333,796 B2 | 12/2012 | Tompkins et al. | |
| 8,597,323 B1 | 12/2013 | Plaza et al. | |
| 8,777,978 B2 | 7/2014 | Strauss et al. | |
| 8,795,316 B2 | 8/2014 | Balgobin et al. | |
| 8,940,011 B2 | 1/2015 | Teoh et al. | |
| 8,945,171 B2 | 2/2015 | Lim | |
| 2002/0002382 A1 | 1/2002 | Wallace et al. | |
| 2002/0165569 A1 | 11/2002 | Ramzipoor et al. | |
| 2004/0002732 A1 | 1/2004 | Teoh et al. | |
| 2005/0149108 A1 | 7/2005 | Cox | |
| 2006/0025802 A1 | 2/2006 | Sowers | |
| 2006/0116714 A1 | 6/2006 | Sepetka et al. | |
| 2006/0276824 A1 | 12/2006 | Mitelberg et al. | |
| 2007/0005081 A1 | 1/2007 | Findlay et al. | |
| 2009/0270901 A1 | 10/2009 | Kelleher et al. | |
| 2009/0297582 A1 | 12/2009 | Meyer et al. | |
| 2010/0121350 A1 | 5/2010 | Mirigian | |
| 2010/0268201 A1 | 10/2010 | Tieu et al. | |
| 2011/0092997 A1 | 4/2011 | Kang | |
| 2011/0213406 A1 | 9/2011 | Aganon et al. | |
| 2012/0071916 A1 | 3/2012 | Kusleika et al. | |
| 2013/0261657 A1 | 10/2013 | Lorenzo | |
| 2013/0325054 A1 | 12/2013 | Watson | |
| 2014/0058434 A1 | 2/2014 | Jones et al. | |
| 2014/0058435 A1 | 2/2014 | Jones et al. | |
| 2014/0277078 A1 | 9/2014 | Slazas et al. | |
| 2014/0277085 A1 | 9/2014 | Mirigian et al. | |

FOREIGN PATENT DOCUMENTS

| | | |
|---|---|---|
| EP | 1806106 A2 | 7/2007 |
| EP | 2777545 A2 | 9/2014 |
| WO | WO-9406503 A1 | 3/1994 |
| WO | WO-01/5836 A1 | 8/2001 |
| WO | WO-2005/032337 A2 | 4/2005 |
| WO | WO-2007070792 A2 | 6/2007 |
| WO | WO-2013081227 A1 | 6/2013 |

OTHER PUBLICATIONS

International Search Report and Written Opinion for International Application No. PCT/US2014/020157, dated Sep. 30, 2014, 16 pages.

International Search Report for PCT/KR2011/009384, dated Dec. 3, 2012, 4 pages.

Invitation to Pay Additional Fees and, Where Applicable, Protest Fee for PCT/US2014/020157, dated Jul. 2, 2014, 7 pages.

Written Opinion for International Application No. PCT/KR2011/009384, dated Dec. 3, 2012, 5 pages.

International Search Report and Written Opinion for International Application No. PCT/US2016/059331, dated Jun. 6, 2017, 22 pages.

* cited by examiner

Step 204

Step 208

Step 212

Step 216

Step 220

Step 224

Step 204

Step 208

Step 212

Step 216

Step 220

Step 224

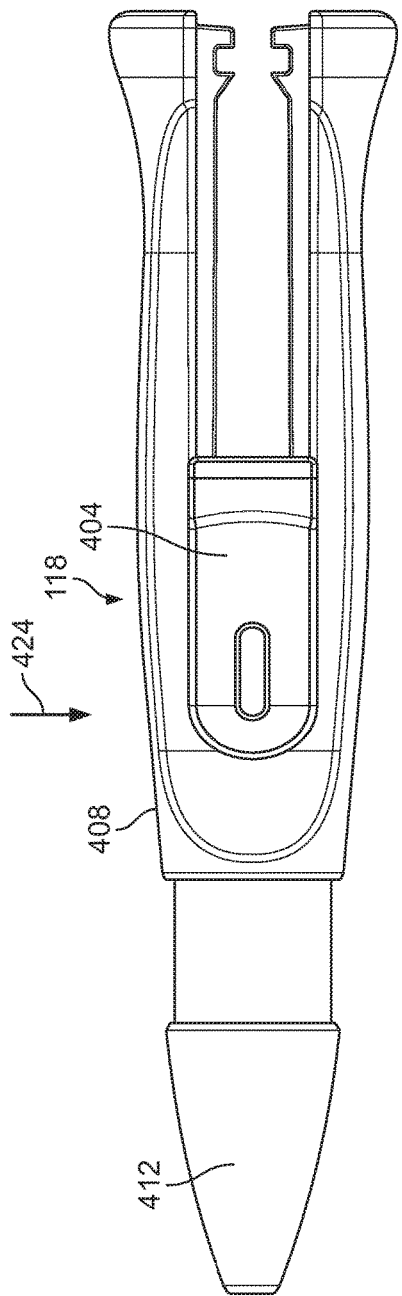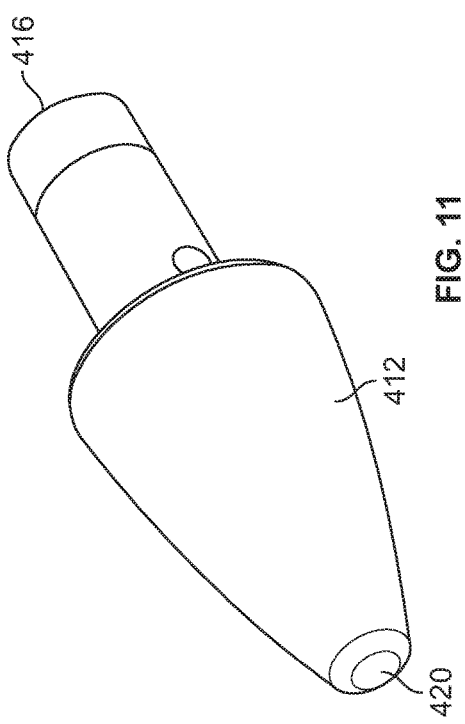
FIG. 10
FIG. 11

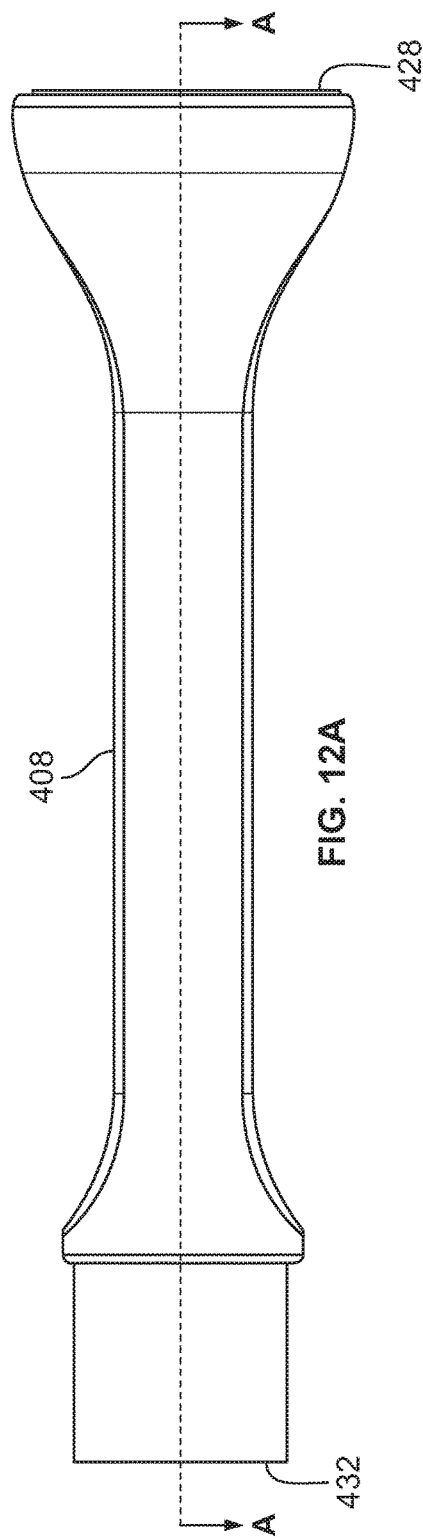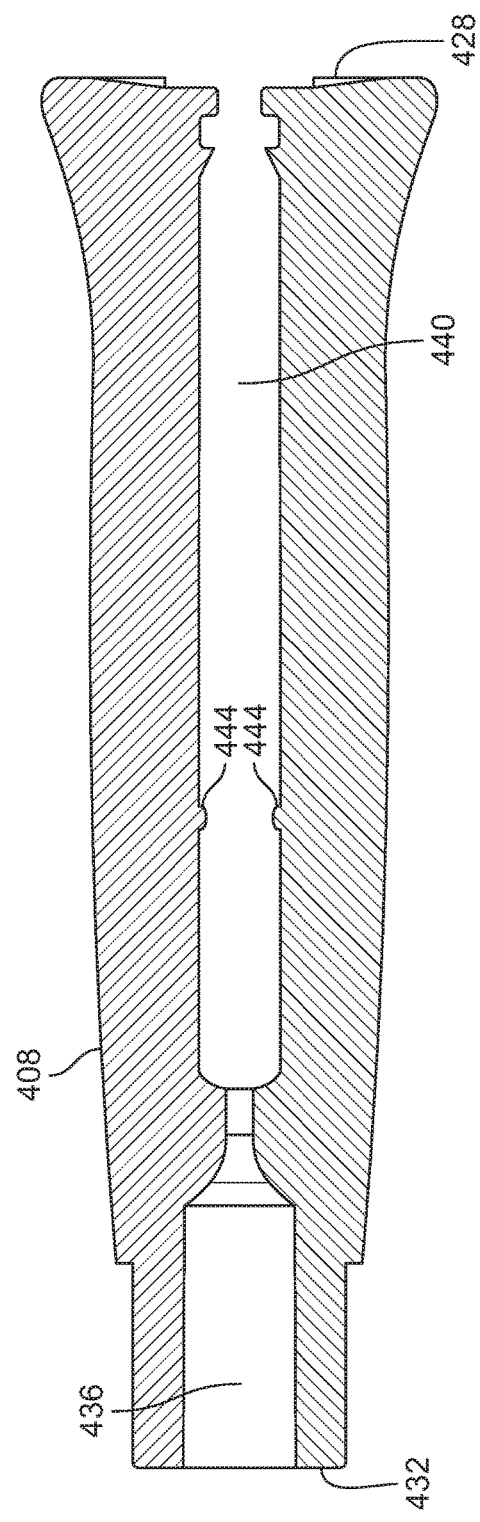

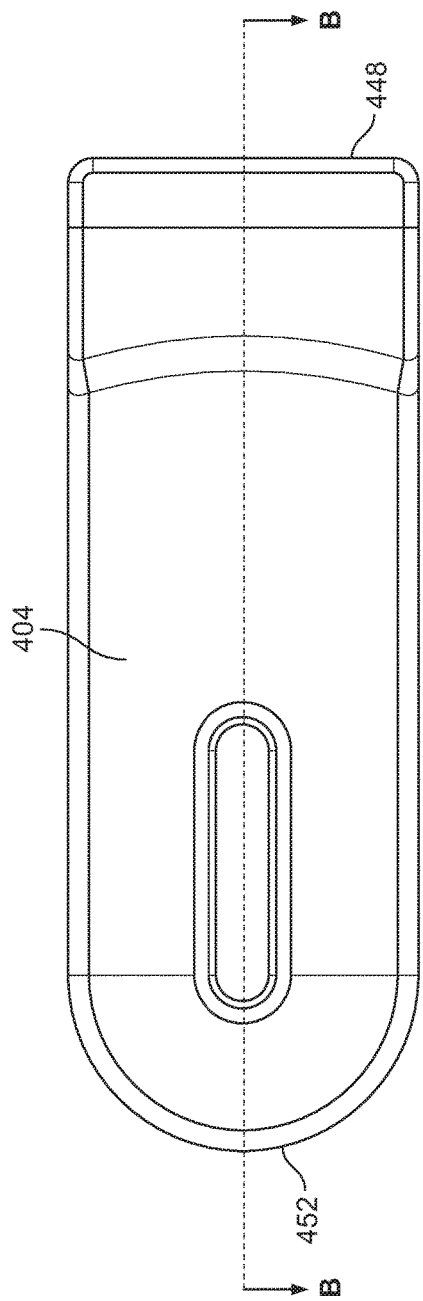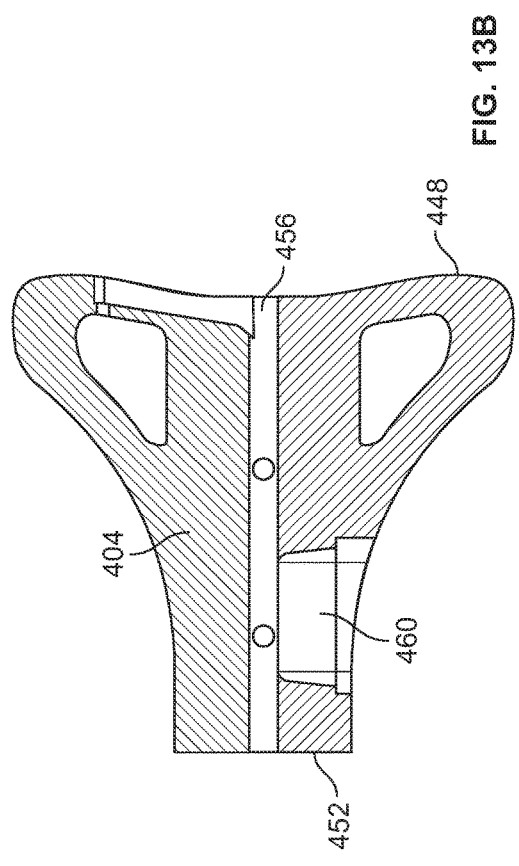

DEVICES AND METHODS FOR DELIVERING AN IMPLANT TO A VASCULAR DISORDER

TECHNICAL FIELD

In various embodiments, the present invention relates to devices and methods for providing therapy to cerebral aneurysms and other similar vascular disorders of a patient in which an implant (e.g., an embolic micro-coil) is controllably delivered to the disorder and mechanically detached from the delivery mechanism for placement within or near the disorder.

BACKGROUND

A cerebral aneurysm (i.e., an acute subarachnoid hemorrhage) is a cerebrovascular swelling on the wall of an artery that develops because of a congenitally weak cerebral artery or due to arteriosclerosis, a bacterial infection, a head wound, brain syphilis, etc. The cerebral aneurysm may develop suddenly without initial symptoms and can cause extreme pain. In general, in 15% of cerebral aneurysm cases, the patient dies suddenly upon development of the cerebral aneurysm. In another 15% of cerebral aneurysm cases, the patient dies under medical treatment and, in 30% of cerebral aneurysm cases, the patient survives after treatment but feels an acute aftereffect. As such, a cerebral aneurysm is a very concerning development.

A cerebral aneurysm may be treated through either an invasive therapy or a non-invasive therapy. Of these, the non-invasive therapy typically fills the cerebral aneurysm with a micro-coil. Generally, filling the cerebral aneurysm with the micro-coil causes blood to clot, prevents an additional inflow of blood, and decreases the risk of a ruptured aneurysm (i.e., an embolization). Advantageously, the non-invasive therapy can ease the aftereffects of brain surgery and can shorten hospitalization time.

The system used in non-invasive therapy typically includes a micro-coil and a delivery pusher for carrying the micro-coil to the patient's cerebral aneurysm. When the micro-coil is properly placed in or near the cerebral aneurysm, an operator (e.g., a physician) separates the micro-coil from the delivery pusher. To initiate detachment of the coil, current micro-coil systems generally require a power supply (for thermal or electrolytic detachment) or a mechanical detachment handle that is attached to the proximal end of the delivery pusher after the coil is positioned in the aneurysm.

Certain mechanical detachment systems employ the use of a wire to retract an element that holds some component of the coil. Certain other mechanical detachment systems use interlocking arms that disengage when advanced beyond a micro-catheter tip, or a ball-screw mechanism that unscrews the coil from a tip of the delivery pusher when the pusher is rotated, or a hydraulic system that ejects the coil from the delivery pusher tip when pressurized with saline.

However, existing schemes for detaching a micro-coil from a delivery pusher often present an unnecessary risk that the micro-coil will be inadvertently released at an incorrect time (e.g., prior to delivery of the micro-coil to the vascular disorder). This can negatively impact the treatment of the patient.

Accordingly, a need exists for improved devices and methods for delivering an implant, such as an embolic micro-coil, to a vascular disorder of a patient, such as a cerebral aneurysm.

SUMMARY OF THE INVENTION

To address the issue of inadvertent detachment and provide a more reliable delivery system, amongst other benefits, various embodiments of the delivery devices described herein feature an improved retention and detachment mechanism having a locked mode and an unlocked mode, to provide reliable retention and prevent inadvertent release of the micro-coil. In particular, embodiments of the invention feature a delivery device having two elongate members (e.g., core wires). An initial refraction of a first elongate member transitions the detachment mechanism from a locked configuration to an unlocked configuration. Further retraction of the first elongate member results in a retraction of the second elongate member. The second elongate member may include a structure at its distal end that urges or positively displaces, as the second elongate member is retracted, the micro-coil or other implant from the delivery device.

In general, in one aspect, embodiments of the invention feature a device for delivering an implant to a vascular disorder of a patient. The device includes a delivery pusher that has a proximal end and distal end and that defines a lumen between the proximal and distal ends, a moveable element defining a passageway therethrough (e.g., a floating tube or a floating coil) that is disposed within the lumen of the delivery pusher, and first and second elongate members (e.g., core wires) that are also disposed within the lumen of the delivery pusher. At least a portion of each of the first and second elongate members passes through the passageway of the moveable element. Movement of the first elongate member in a first direction causes a time-delayed movement of the second elongate member in the same (i.e., first) direction using, for example, a lost motion coupling or mechanism.

Various embodiments of this aspect of the invention include the following features. The first elongate member may be configured to lock the implant to prevent release of the implant from the delivery pusher. Movement of the first elongate member in the first direction may unlock the implant, thereby permitting release of the implant from the delivery pusher. Movement of the first elongate member in the first direction may also cause a movement of the moveable element in the first direction. In one embodiment, a bumper element (e.g., a tube or a coil) is coupled to the first elongate member. In such a case, the bumper element may be adapted to move the moveable element in the first direction when the first elongate member is moved in the first direction.

In another embodiment, a bumper element (e.g., a tube or a coil) may also be coupled to the second elongate member. In this case, the moveable element may be adapted to move the bumper element (and, thus, the second elongate member) in the first direction when the first elongate member is moved in the first direction. In yet another embodiment, an element for displacing the implant from the delivery pusher is coupled to a distal end of the second elongate member. The displacing element may have a tapered or curved surface.

In general, in another aspect, embodiments of the invention feature a method for delivering an implant (e.g., an embolic coil) to a vascular disorder of a patient. In accordance with the method, the implant may be advanced in proximity to the vascular disorder via a delivery pusher that has a proximal end and a distal end and that defines a lumen between the proximal and distal ends. Then, a first elongate member (e.g., a core wire) may be moved in a first direction within the lumen of the delivery pusher. As before, at least a portion of each of the first elongate member and a second elongate member (which may also be a core wire) may pass through a passageway of a moveable element (e.g., a floating tube or a floating coil) disposed within the lumen of the delivery pusher. The movement of the first elongate member in the first direction causes a time-delayed movement of the second elongate member in the same (i.e., first) direction with the lumen of the delivery pusher so as to release the implant from the delivery pusher.

In various embodiments, the implant is locked to the delivery pusher prior to the step of moving the first elongate member in the first direction. Moving the first elongate member in the first direction then unlocks the implant, thereby permitting release of the implant from the delivery pusher. As before, moving the first elongate member in the first direction also moves the moveable element in the first direction, and movement of the moveable element in the first direction operates to move the second elongate member in the first direction. In one embodiment, the implant also includes a proximal tab or a suture loop that is adapted to couple a proximal end of the implant's embolic coil to the distal end of the delivery pusher.

In general, in yet another aspect, embodiments of the invention feature a device for delivering an implant to a vascular disorder of a patient. The device includes a delivery pusher that has a proximal end and distal end and that defines a lumen between the proximal and distal ends, a detachment handle, and a first elongate member (e.g. a core wire). The detachment handle is coupled to the proximal end of the delivery pusher and may be used to initiate a mechanical release of an implant coupled to the distal end of the delivery pusher when the implant is placed in proximity to a vascular disorder using, for example, a lost motion coupling or mechanism. The detachment handle may also include an engagement mechanism that defines a second lumen (e.g., a hypotube). For its part, the first elongate member extends from a distal end of the first lumen, along the first and second lumens, and beyond a proximal end of the engagement mechanism by a first distance, thereby allowing the engagement mechanism to move towards a proximal end of the first elongate member by the first distance prior to engaging the proximal end of the first elongate member.

In various embodiments of this aspect of the invention, the detachment handle also includes a handle slider. The engagement mechanism may be disposed within the handle slider. In addition, an engagement member (e.g., a coil or a tube) may be coupled to the proximal end of the first elongate member.

In general, in still another aspect, embodiments of the invention feature a method for delivering an implant (e.g., an embolic coil) to a vascular disorder of a patient. In accordance with the method, the implant may be advanced in proximity to the vascular disorder via a delivery pusher that has a proximal end and a distal end and that defines a lumen between the proximal and distal ends. The delivery pusher may also be coupled at its proximal end to a detachment handle and at its distal end to the implant. As before, the detachment handle may include an engagement mechanism that defines a second lumen (e.g., a hypotube). According to the method, at least a portion of the detachment handle (e.g., a handle slider) may be manipulated so that the engagement mechanism engages a proximal end of a first elongate member (e.g., a core wire), thereby initiating a mechanical release of the implant from the distal end of the delivery pusher. The first elongate member extends from a distal end of the first lumen, along the first and second lumens, and beyond a proximal end of the engagement mechanism by a first distance prior to being engaged by the engagement mechanism, thereby allowing the engagement mechanism to move towards the proximal end of the first elongate member by the first distance prior to engaging the proximal end of the first elongate member.

In one embodiment of this aspect of the invention, the engagement mechanism is disposed within the handle slider. In another embodiment, the implant includes a proximal tab or a suture loop that is adapted to couple a proximal end of the implant's embolic coil to the distal end of the delivery pusher.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 10 is a schematic side view of a detachment handle of the delivery device depicted in FIG. 1 in accordance with one embodiment of the invention;

FIG. 11 is a schematic perspective view of a handle body nose of the detachment handle depicted in FIG. 10 in accordance with one embodiment of the invention;

FIG. 12A is a schematic top view of a handle body of the detachment handle depicted in FIG. 10 in accordance with one embodiment of the invention;

FIG. 12B is a schematic cross-sectional view taken along line A-A of the handle body depicted in FIG. 12A;

FIG. 13A is a schematic side view of a handle slider of the detachment handle depicted in FIG. 10 in accordance with one embodiment of the invention;

FIG. 13B is a schematic cross-sectional view taken along line B-B of the handle slider depicted in FIG. 13A.

DESCRIPTION

Figure 1:
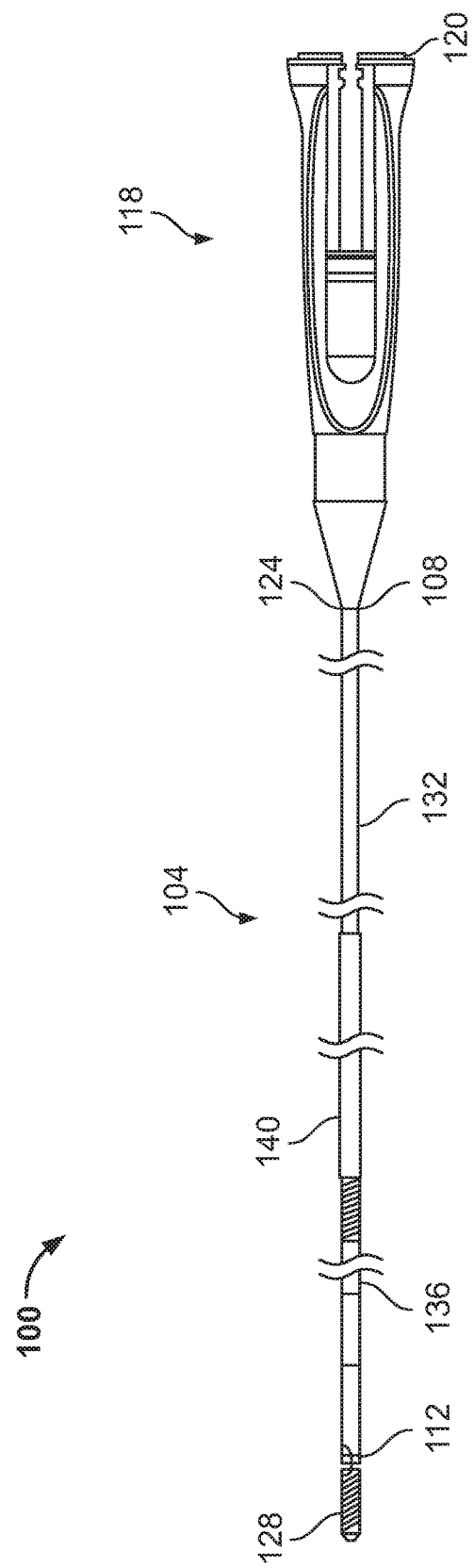
FIG. 1 schematically illustrates a device for delivering an implant to a vascular disorder of a patient in accordance with one embodiment of the invention.

In broad overview, embodiments of the present invention feature a device for delivering an implant (e.g., an embolic micro-coil) to a vascular disorder of a patient, such as a cerebral aneurysm. FIG. 1 schematically depicts the delivery device 100 in accordance with one embodiment of the invention. As illustrated, the delivery device 100 includes a delivery pusher 104 having a proximal end 108 and a distal end 112. The delivery pusher 104 defines a lumen 116 (see FIG. 2) between the proximal and distal ends 108, 112. With reference still to FIG. 1, the delivery device 100 also includes a detachment handle 118 having a proximal end 120 (i.e., an end 120 closest to an operator of the delivery device 100) and a distal end 124. The distal end 124 of the detachment handle 118 is coupled to the proximal end 108 of the delivery pusher 104. In use, an implant 128 is coupled to the distal end 112 of the delivery pusher 104 in, for example, one of the manners described below. As also described below, the detachment handle 118 is operated by a user to mechanically release the implant 128 from the delivery pusher 104 when the implant 128 is placed in proximity to (e.g., near or within) the vascular disorder to be treated.

As also shown in FIG. 1, the delivery pusher 104 includes a rigid proximal shaft 132 and a flexible distal shaft that includes a flexible inner shaft 136 and a flexible outer shaft 140. The proximal shaft 132 may be made from rigid, metal hypotube, for example 300 series stainless steel with a wall thickness of about 0.002" to provide good structural integrity during implant 128 delivery and stability during detachment actuation. The flexible inner shaft 136 and flexible outer shaft 140 may each be made from a rigid thin-walled polymer (e.g., PEEK with a wall thickness of about 0.001"), to permit bending and deflection to properly position the implant 128 proximate the vascular disorder.

Figure 2:
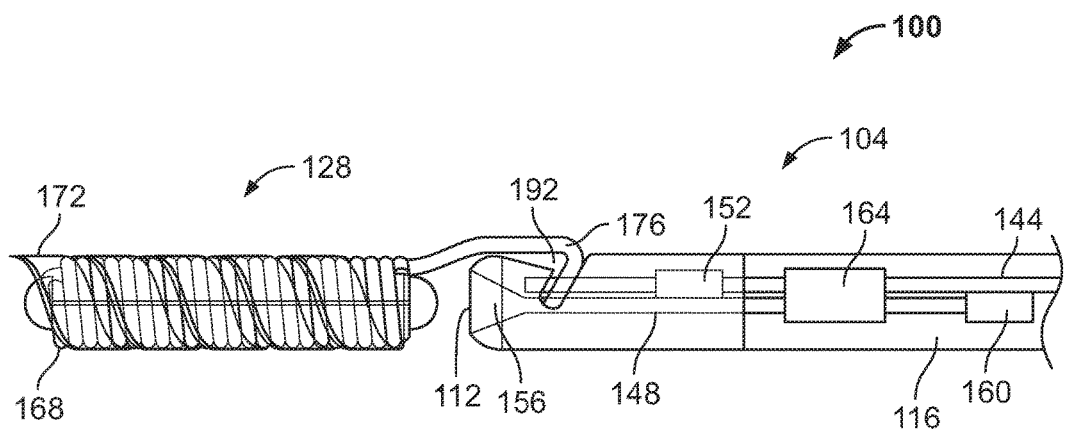
FIG. 2 schematically illustrates a distal end portion of the delivery device depicted in FIG. 1 in accordance with one embodiment of the invention.

FIG. 2 schematically illustrates a distal end portion of the delivery device 100 in accordance with one embodiment of the invention. As shown, the delivery device 100 includes first and second elongate members 144, 148 disposed within the lumen 116 of the delivery pusher 104. Each elongate member 144, 148 may be, for example, a core wire (e.g., 300 series stainless steel). Each core wire 144, 148 may be ground on its distal end and be coated on its unground section with, for example, polytetrafluoroethylene (PTFE) to reduce friction. Each core wire 144, 148 may be about 0.006" in diameter, and ground to about 0.002" at its distal tip.

In one embodiment, the first elongate member 144 extends from a distal end of the lumen 116 defined by the delivery pusher 104, along the lumen 116, out the proximal end 108 of the delivery pusher 104, and into and through a lumen defined within the detachment handle 118, as further described below. As shown, a first bumper element 152 may be coupled (e.g., soldered, welded, adhered using an ultraviolet (uv) light curing or other adhesive, swaged, crimped, or otherwise fixed using a known technique) to the first elongate member 144 near its distal end. The first bumper element 152 may be, for example, a tube, a coil, or any other structure capable of transmitting force and motion to additional component(s), as further described herein. In one embodiment, the second elongate member 148 is shorter in length than the first elongate member 144. As shown, a displacing element 156 (e.g., a conical or bell-shaped tip having a tapered surface) for displacing a proximal tab 176 of the implant 128 from the delivery pusher 104 may be coupled to a distal end of the second elongate member 148. The second elongate member 148 may extend proximally from the displacing element 156 and may terminate within the distal portion of the delivery device 100. In particular, the second elongate member 148 may be coupled (e.g., soldered, welded, adhered using an ultraviolet (uv) light curing or other adhesive, swaged, crimped, or otherwise fixed using a known technique) at its proximal end to a second bumper element 160. As with the first bumper element 152, the second bumper element 160 may be a tube, a coil, or any other structure capable of receiving force from additional component(s) to cause motion of the second elongate member 148, as further described herein.

In one embodiment, the displacing element 156 and the second bumper element 160 are sized to fit snugly against the inner wall of the delivery pusher 104 that defines the lumen 116 (i.e., the displacing element 156 and the second bumper element 160 may each have an outer diameter approximately equal to (or just slightly less than) an inner diameter of the delivery pusher 104). As such, there is enough frictional forces to keep the displacing element 156 and the second bumper element 160 (and, thus, the second elongate member 148) from moving around during the process of delivering the implant 128 to the vascular disorder, but the displacing element 156 and the second bumper element 160 remain loose enough so that they (and, thus, the second elongate member 148) may be easily moved when the first elongate member 144 is retracted to release the implant 128 from the distal end 112 of the delivery pusher 104, as further described below.

As also illustrated in FIG. 2, a moveable element 164 may also be disposed within the lumen 116 of the delivery pusher 104. The moveable element 164 may be a floating tube, a floating coil, or any other structure capable of receiving and transmitting force and motion as described herein. In particular, in one embodiment, a passageway (e.g., a lumen) is defined through the moveable element 164 from its distal to proximal ends, and at least a portion of each of the first and second elongate members 144, 148 passes through that passageway.

Initially, the implant 128 is coupled to the distal end 112 of the delivery pusher 104. The exemplary implant 128 depicted in FIG. 2 is a covered embolic coil. In particular, the implant 128 includes an embolic micro-coil 168 and a cover 172 that is wound around the micro-coil 168. The covered embolic coil 128 may be, for example, of the type described in commonly-owned U.S. patent application Ser. No. 14/808,550 entitled "Covered Embolic Coils," the disclosure of which is hereby incorporated herein by reference in its entirety. As will be understood by one of ordinary skill in the art, however, other implants may also be delivered using the delivery device 100. As shown in FIG. 2, a proximal tab 176 of the cover 172 couples the covered embolic coil 128 to the distal end 112 of the delivery pusher 104.

Figure 3:
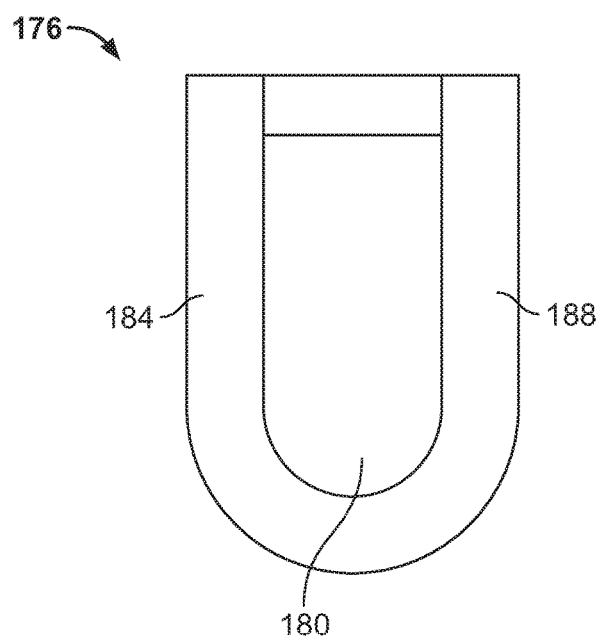
FIG. 3 is a schematic front end view of a proximal tab for coupling an implant to a device for delivering the implant to a vascular disorder of a patient in accordance with one embodiment of the invention.
Figure 4A:
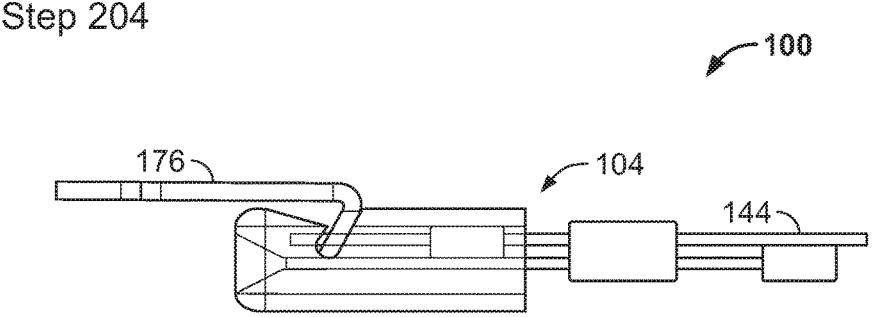
FIGS. 4A-4F schematically illustrate the steps in one exemplary method for releasing an implant from a device that has delivered the implant to a vascular disorder of a patient in accordance with one embodiment of the invention.
Figure 4B:
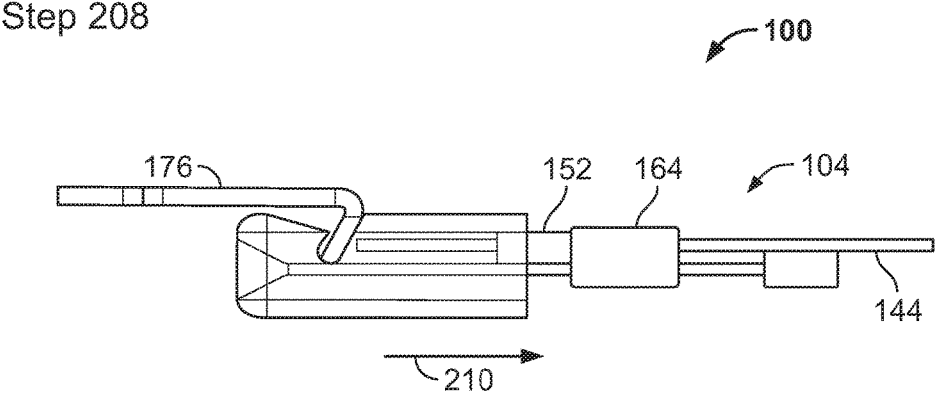
Figure 4C:
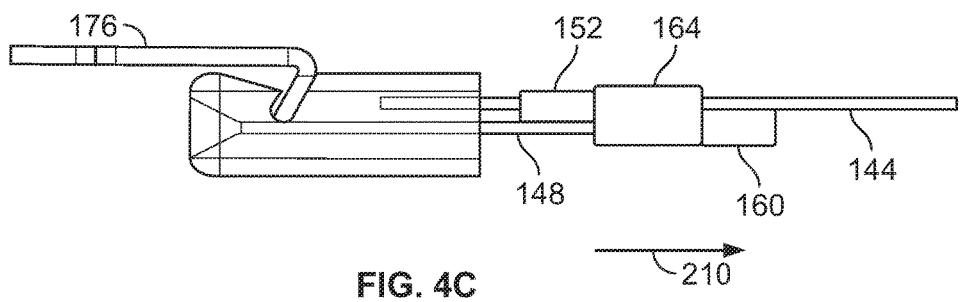
Figure 4D:
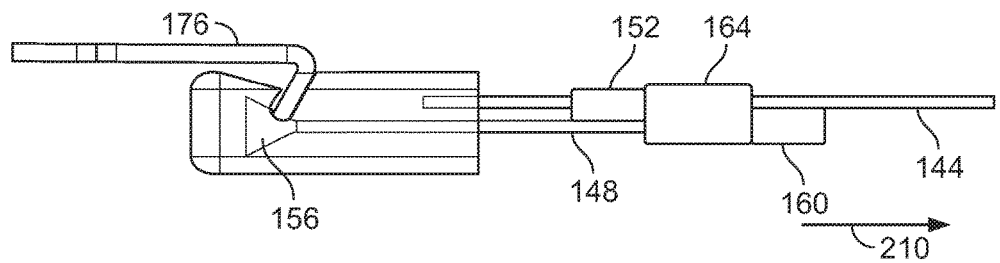
Figure 4E:
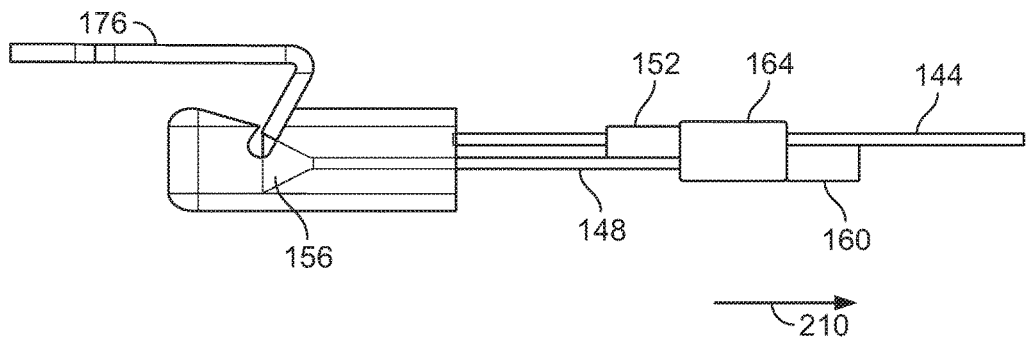
Figure 4F:
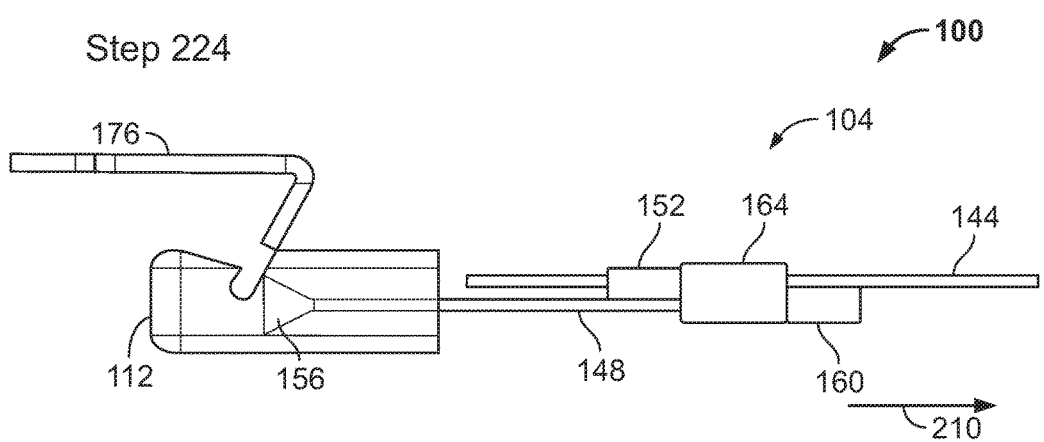
Figure 5A:
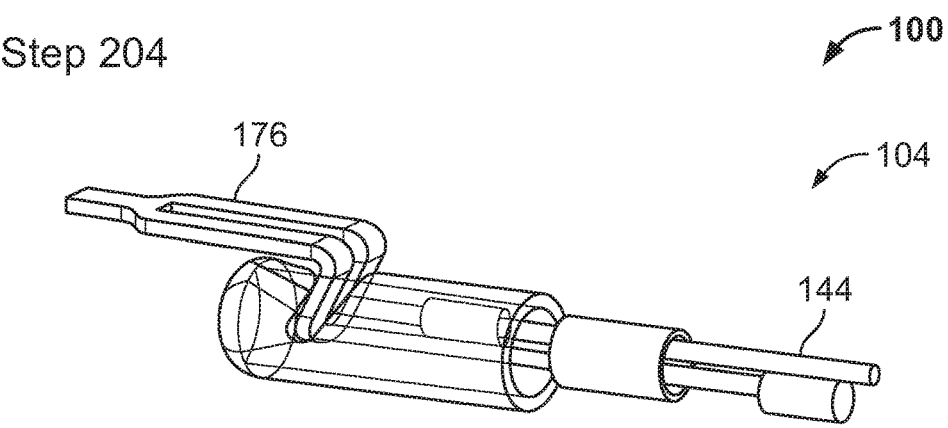
FIGS. 5A-5F schematically illustrate perspective views of the exemplary steps of the method depicted in FIGS. 4A-4F, respectively.
Figure 5B:
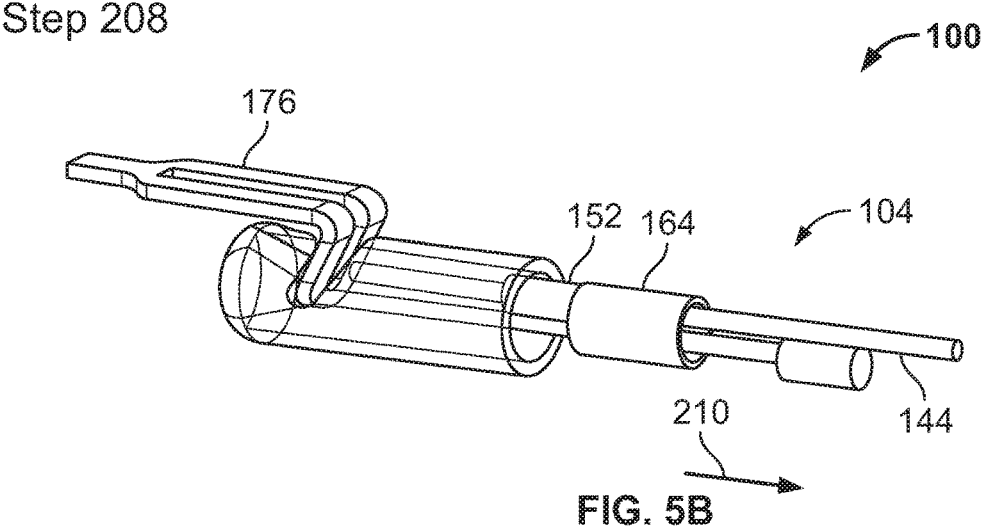
Figure 5C:
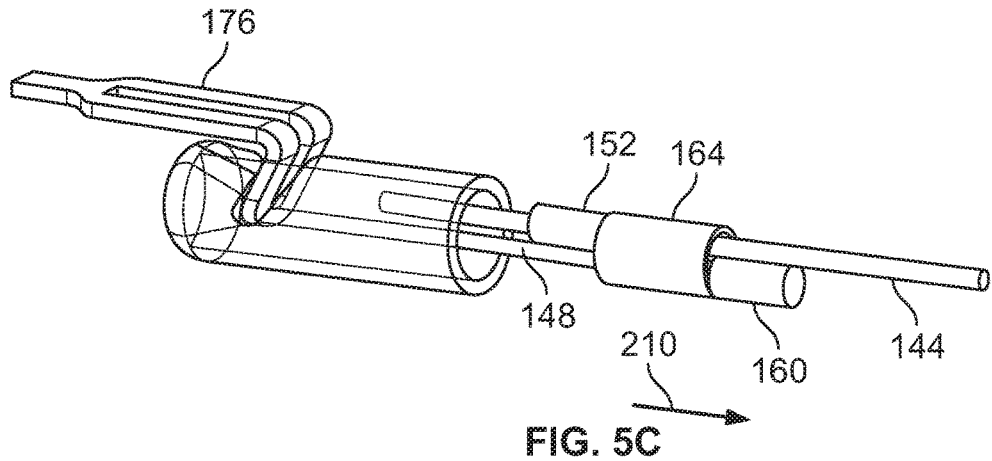
Figure 5D:
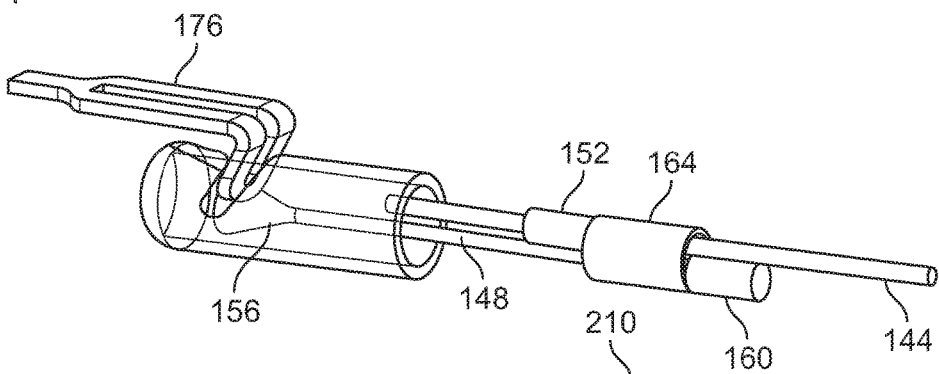
Figure 5E:
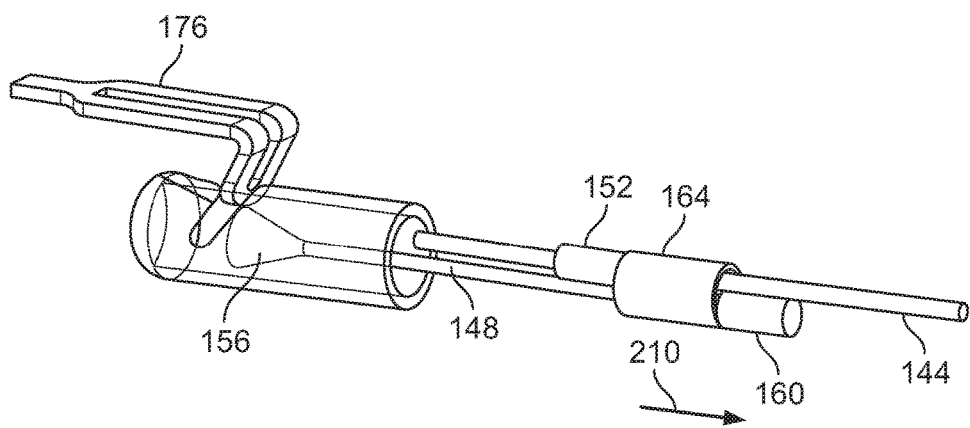
Figure 5F:
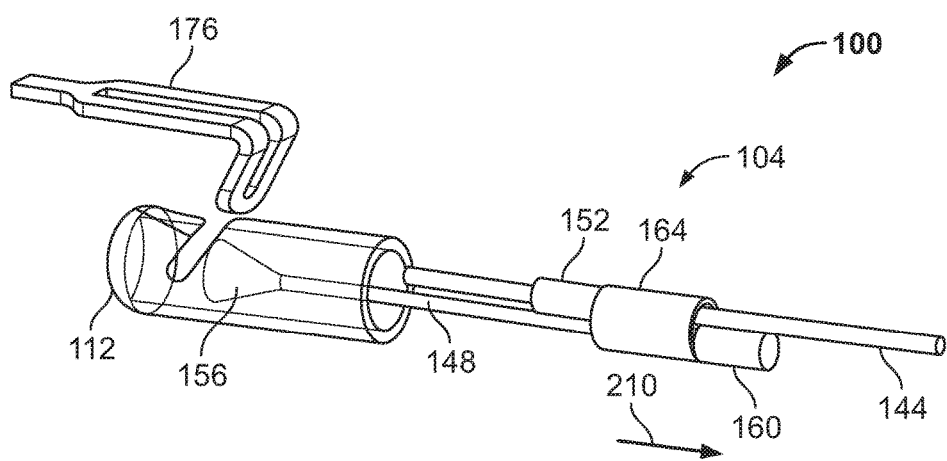

The proximal tab 176 is shown from its side in FIG. 2. A front end view of one embodiment of the proximal tab 176 is depicted in FIG. 3, while FIGS. 5A-5F depict perspective views of the proximal tab 176. With reference to FIG. 3, the proximal tab 176 may be generally U-shaped, and may include an aperture 180 formed between its two legs 184, 188.

Referring again to FIG. 2, in one embodiment, a notch 192 is formed within a sidewall of the delivery pusher 104 at its distal end 112. The covered embolic coil 128 may thus be attached to the delivery pusher 104 by, for example, positioning the proximal tab 176 within the notch 192 and locking the proximal tab 176 in place by passing the first elongate member 144 through the aperture 180 of the proximal tab 176. Once it passes through the aperture 180, the distal end of the first elongate member 144 may itself be secured in place by being tucked under a distal edge of the notch 192. Alternatively, the distal end of the first elongate member 144 may be secured in place by being wedged between the displacing element 156 and an inner surface of the delivery pusher 104. In these ways, the first elongate member 144 is configured to lock the covered embolic coil 128 (or another implant 128 featuring a connecting member similar in function to the proximal tab 176) in place to prevent inadvertent release of the covered embolic coil 128 from the delivery pusher 104.

FIGS. 4A-4F schematically illustrate the steps in one exemplary method for releasing the implant 128 from the delivery pusher 104 of the delivery device 100, while FIGS. 5A-5F schematically illustrate perspective views of those same steps. Note that, for ease of illustration, only the proximal tab 176 of the implant 128 is depicted in FIGS. 4A-4F and in FIGS. 5A-5F. In practice, however, the remainder of the implant 128 (e.g., the embolic micro-coil 168 and its cover 172) would also be present (e.g., with the proximal tab 176 coupled to and extending from the cover 172). Initially, at step 204, the implant 128 is locked to the delivery pusher 104 via a coupling of the proximal tab 176 with the first elongate member 144, as just described. At step 208, the first elongate member 144 is moved in a first direction within the lumen 116 of the delivery pusher 104. In particular, the first elongate member 144 is retracted in the direction indicated by arrow 210 until the first bumper element 152 abuts the moveable element 164. This movement of the first elongate member 144 unlocks the first elongate member 144 from the implant 128 (e.g., withdraws the distal end of the first elongate member 144 from the aperture 180 of the proximal tab 176), thereby readying the implant 128 for release from the delivery pusher 104. Movement of the first elongate member 144 in the direction indicated by the arrow 210 may be accomplished through operator (e.g., physician) manipulation of the detachment handle 118, as further described below.

Continued retraction of the first elongate member 144 in the direction of the arrow 210 causes the first bumper element 152 of the first elongate member 144 to move the moveable element 164 into contact with the second bumper element 160 of the second elongate member 148, as shown at step 212. Both the moveable element 164 and the second bumper element 160 are thereby serially engaged by the first bumper element 152. Due to this series abutment of the first bumper element 152, the moveable element 164, and the second bumper element 160, as the operator continues to retract, at step 216, the first elongate member 144 and the first bumper element 152 in the direction of the arrow 210, the second elongate member 148 is also caused to retract in the direction of the arrow 210. This resulting movement of the second elongate member 148 in the direction indicated by the arrow 210 causes the conical or bell-shaped displacing element 156 to engage a bottom edge of the proximal tab 176 of the implant 128. Then, as illustrated at step 220, continued retraction of the first elongate member 144 (and, consequently, of the second elongate member 148) in the direction of the arrow 210 pushes radially outwardly the proximal tab 176 of the implant 128 along the angled slope of the conical or bell-shaped displacing element 156 until, as illustrated at step 224, the proximal tab 176 (and thus the implant 128) is released from the distal end 112 of the delivery pusher 104.

Accordingly, as can be appreciated from FIGS. 4A-4F and 5A-5F and the description above, movement of the first elongate member 144 in the direction indicated by the arrow 210 within the lumen 116 of the delivery pusher 104 results in a consequent time-delayed movement of the second elongate member 148 in the same direction within the lumen 116 of the delivery pusher 104, so as to release the implant 128 from the delivery pusher 104. The initial longitudinal gaps or spacings between the first bumper element 152, the moveable element 164, and the second bumper element 160 provide the lost motion sequence of unlocking the proximal tab 176 and thereafter forcefully displacing the proximal tab 176 to release the implant 128, but only after moving the first elongate member 144 a distance sufficient to eliminate all of the gaps between the abutting elements 152, 164, 160. The interaction of the first and second elongate members 144, 148 through the first bumper element 152, the moveable element 164, and the second bumper element 160 is entirely transparent to the operator, who focuses solely on retracting the first elongate member 144 in the direction indicated by the arrow 210. In another embodiment, the moveable element 164 is eliminated and the first bumper element 152 may contact the second bumper element 160 directly, after the gap therebetween is eliminated.

Figure 6:
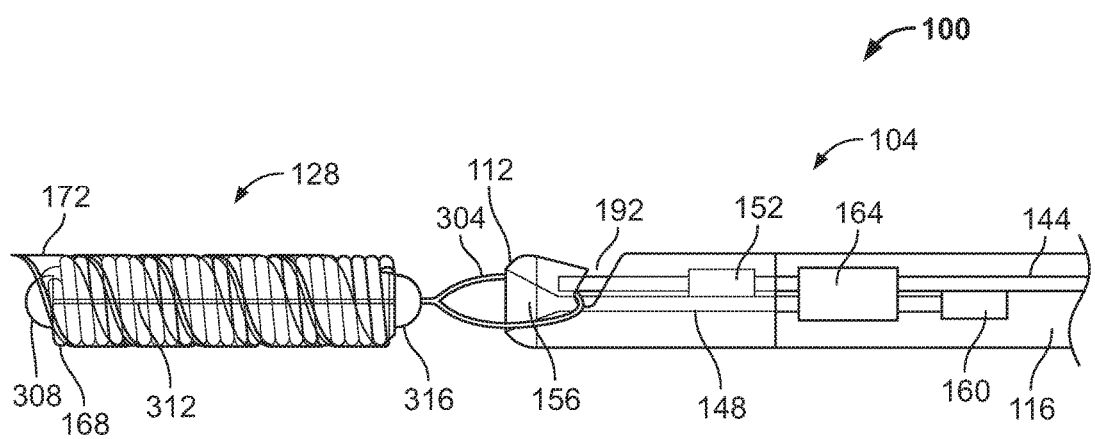
FIG. 6 schematically illustrates a distal end portion of the delivery device depicted in FIG. 1 in accordance with another embodiment of the invention.
Figure 7:
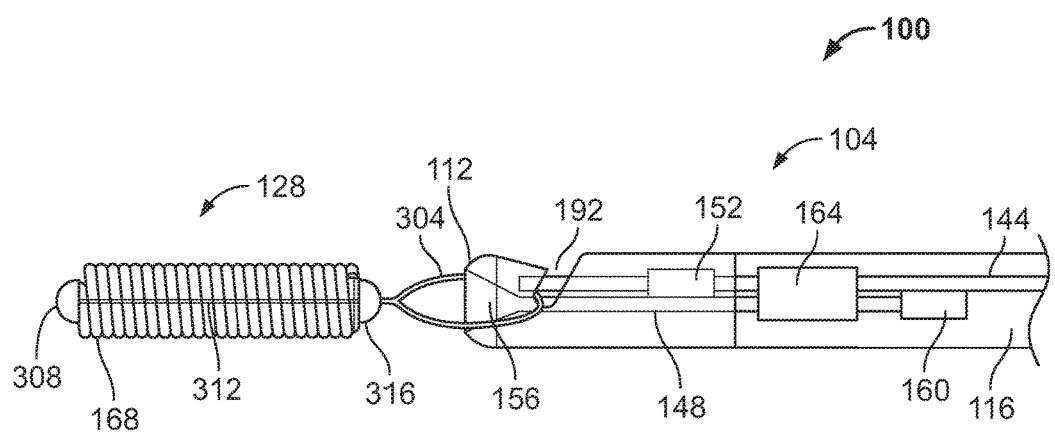
FIG. 7 schematically illustrates a distal end portion of the delivery device depicted in FIG. 1 in accordance with yet another embodiment of the invention.

Instead of being attached to the delivery pusher 104 via the proximal tab 176, the implant 128 may be attached to (and released from) the delivery pusher 104 of the above-described delivery device 100 via any of a variety of other structures. One such structure is illustrated in FIGS. 6 and 7. In particular, the implant 128 depicted in FIG. 6 is the covered embolic coil mentioned above (i.e., including the cover 172 wound around the embolic micro-coil 168), while the implant 128 depicted in FIG. 7 features the embolic micro-coil 168 without a corresponding cover. In both cases, the implant 128 includes a suture loop 304 held in place in the notch 192 at the distal end 112 of the delivery pusher 104 by the first elongate member 144. More specifically, both implants 128 depicted in FIGS. 6 and 7 include a ball of suture 308 secured (e.g., melted or knotted) to a distal end of the embolic micro-coil 168, a length of suture 312 extending between the distal and proximal ends of the embolic micro-coil 168, a proximal fixation of suture 316 secured (e.g., melted or knotted) to the proximal end of the embolic micro-coil 168, and the suture loop 304 adjacent to and extending from the proximal fixation of suture 316. The ball of suture 308, the length of suture 312, the proximal fixation of suture 316, and the suture loop 304 may be made from a polymer material, such as polypropylene. In one embodiment, the release of the suture loop 304 from the notch 192 at the distal end 112 of the delivery pusher 104 is accomplished by following the same steps described above with reference to FIGS. 4A-4F and 5A-5F.

Figure 8:
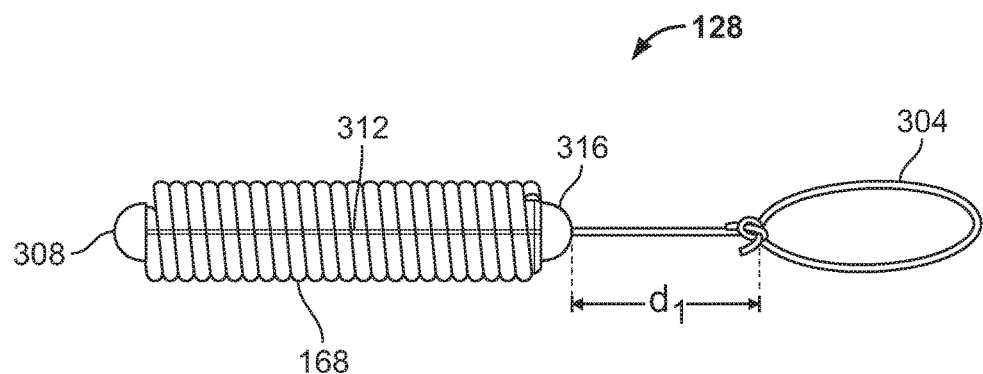
FIG. 8 schematically illustrates an implant in accordance with one embodiment of the invention.
Figure 9:
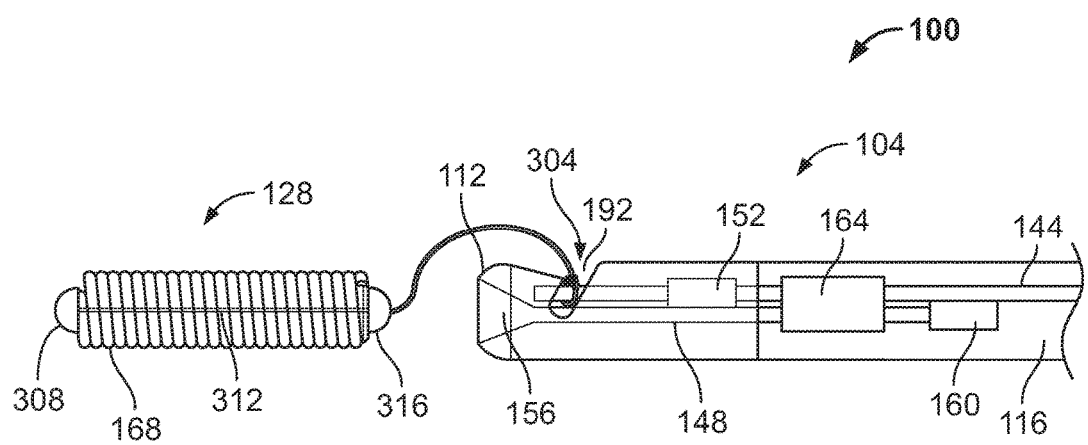
FIG. 9 schematically illustrates a distal end portion of the delivery device depicted in FIG. 1 in accordance with still another embodiment of the invention.

FIG. 8 schematically depicts an alternative embodiment of the implant 128. In this embodiment, the suture loop 304 is created by knotting the suture at a distance $d_1$ from the proximal fixation of suture 316, rather than beginning the suture loop 304 adjacent to the proximal fixation of suture 316 as in the embodiments depicted in FIGS. 6 and 7. As will be understood by one of ordinary skill in the art, the suture loop 304 can be created in a variety of locations, sizes, and manners. For example, FIG. 9 depicts yet another embodiment in which a small suture loop 304 is knotted and locked to the distal end 112 of the delivery pusher 104 by being placed around the first elongate member 144.

As mentioned previously, in one embodiment, the operator of the delivery device 100 retracts the first elongate member 144, and thereby releases the implant 128 from the distal end 112 of the delivery pusher 104, by manipulating the detachment handle 118. FIG. 10 is a side view of the detachment handle 118 according to one embodiment of the invention. As illustrated, the detachment handle 118 includes a handle slider 404, a handle body 408, and a handle body nose 412. FIG. 11 is a perspective view of the handle body nose 412 according to one embodiment of the invention. The handle body nose 412 includes a proximal end 416 and a distal end 420, and defines a lumen between the proximal and distal ends 416, 420. In one embodiment, the proximal shaft 132 of the delivery pusher 104 (see FIG. 1) is connected to the handle body nose 412 by inserting the proximal shaft 132 into the lumen of the handle body nose 412 at its distal end 420 and by applying an adhesive, press fitting the connection, securing the connection with a mechanical fastener (e.g., a set screw), employing a threaded connection, etc.

FIG. 12A is a top view of the handle body 408 (i.e., a view of the handle body 408 looking in the direction of arrow 424 in FIG. 10) according to one embodiment of the invention, while FIG. 12B is a cross-sectional view of the handle body 408 taken along line A-A depicted in FIG. 12A. As illustrated, the handle body 408 includes a proximal end 428, a distal end 432, a cavity 436 at the distal end 432 for receiving the proximal end 416 of the handle body nose 412, and a track 440 running the majority of the handle body 408 to the proximal end 428 and along which the handle slider 404 may be moved. The handle body 408 also includes detent features 444, which hold the handle slider 404 in place prior to the handle slider 404 being manipulated (e.g., retracted) by the operator of the delivery device 100.

FIG. 13A is a side view of the handle slider 404 according to one embodiment of the invention, while FIG. 13B is a cross-sectional view of the handle slider 404 taken along line B-B depicted in FIG. 13A. As illustrated, the handle slider 404 includes a proximal end 448 and a distal end 452, and defines a lumen 456 that extends between the proximal and distal ends 448, 452. In addition, the handle slider 404 defines a side slot 460 into which an adhesive may be inserted to secure an additional structure placed within the lumen 456.

Figure 14:
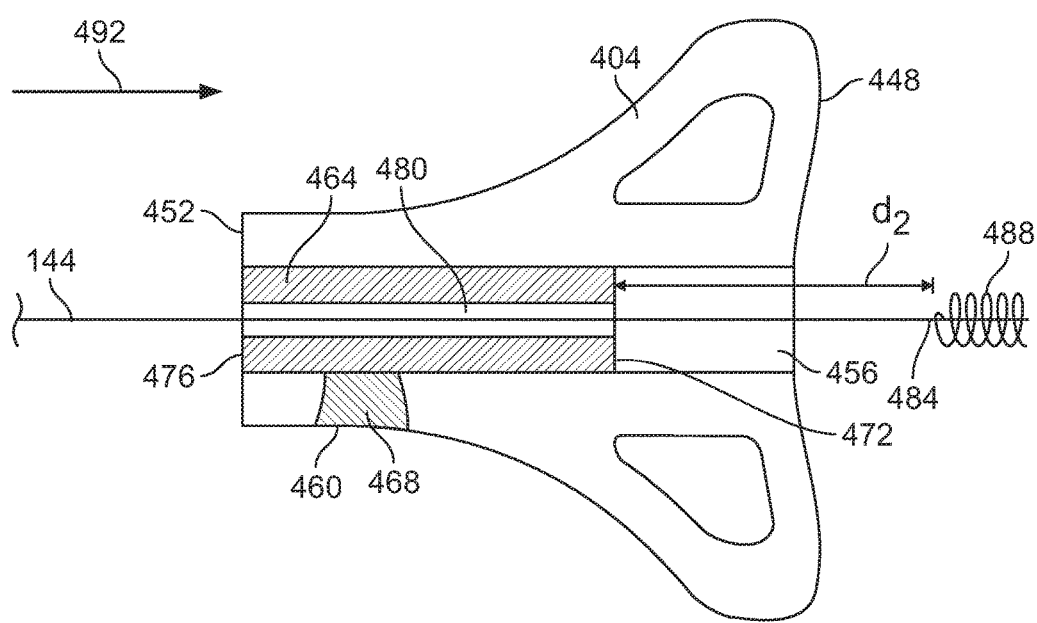
FIG. 14 schematically illustrates additional components assembled within the handle slider depicted in FIGS. 13A and 13B in accordance with one embodiment of the invention.

FIG. 14, for example, depicts an engagement mechanism 464 housed within the lumen 456 of the handle slider 404 and secured to the handle slider 404 by an ultraviolet (uv) light curing or other adhesive 468 inserted into the side slot 460. Other retention schemes may also be employed. The engagement mechanism 464 may be, for example, a hypotube that includes a proximal end 472 and a distal end 476, and that defines a lumen 480 between the proximal and distal ends 472, 476. The lumen 480 may be sized to receive therethrough the first elongate member 144 in a sliding fit.

The first elongate member 144 extends through the lumens 456, 480 of the handle slider 404 and engagement mechanism 464. In greater detail, the first elongate member 144 extends from a distal end of the delivery pusher lumen 116, along the delivery pusher lumen 116, out the proximal end 108 of delivery pusher 104, into the distal end 420 of the handle body nose 412, out the proximal end 416 of the handle body nose, into the lumens 456, 480 of the handle slider 404 and engagement mechanism 464 at their distal ends 452, 476, along the lumens 456, 480 of the handle slider 404 and engagement mechanism 464, and out the proximal ends 472, 448 of the engagement mechanism 464 and handle slider 404. In particular, as illustrated in FIG. 14, a proximal end 484 of the first elongate member 144 extends beyond the proximal end 472 of the engagement mechanism 464 by a distance $d_2$ for the reason explained below.

In one embodiment, an engagement member 488 is coupled to or formed at the proximal end 484 of the first elongate member 144. The engagement member 488 may be a coil (as illustrated), a tube, a disc, or any other enlarged structure adapted to abut the proximal end 172 of the engagement mechanism 464. The engagement member 488 may be, for example, soldered, welded, adhered using an ultraviolet (uv) light curing or other adhesive, swaged, crimped, or otherwise coupled using a known technique to or formed at the proximal end 484 of the elongate member 144. In one embodiment, an outer diameter or dimension of the engagement member 488 is less than an inner diameter of the lumen 456 of the handle slider 404, but greater than an inner diameter of the lumen 480 of the engagement mechanism 464. In this way, the engagement member 488 is free to slide into the lumen 456 of the handle slider 404 (or, equivalently, the handle slider 404 is free to slide over the first elongate member 144 and engagement member 488) until the engagement member 488 abuts the engagement mechanism 464.

With reference again to FIG. 1, although the flexible inner shaft 136 and flexible outer shaft 140 utilize relatively rigid polymer members (for stability during mechanical detachment of the implant 128), they also need to provide enough flexibility and low-friction to access the desired neurovascular site through a tortuous micro-catheter. As such, the flexible inner shaft 136 and flexible outer shaft 140 are more susceptible to elongation than the metal proximal shaft 132 or the first elongate member 144. Since, during delivery of the implant 128 and as described above, the distal end of the first elongate member 144 is secured in place by being tucked under the distal edge of the notch 192 and/or wedged between the displacing element 156 and the inner surface of the delivery pusher 104 (and, thus, the first elongate member 144 and delivery pusher 104 are connected during delivery of the implant 128), if the delivery device 100 encounters friction during access to the vascular disorder, the metal proximal shaft 304 and the first elongate member 144 will likely retract at the same rate, but the assembly of the flexible inner shaft 136 and flexible outer shaft 140 will elongate at a greater rate. If the assembly of the flexible inner shaft 136 and flexible outer shaft 140 elongates at a greater rate than the first elongate member 144 and proximal shaft 132, the detachment handle 118 will in effect move proximally, towards the engagement member 488 depicted in FIG. 14.

To avoid engaging the engagement member 488 at the proximal end 484 of the first elongate member 144 with the engagement mechanism 464 located within the handle slider 404 and to avoid prematurely (and thus undesirably) detaching the implant 128 from the delivery pusher 108 when friction is encountered during delivery of the implant 128 to the vascular disorder, the proximal end 484 of the first elongate member 144 is designed to extend beyond the proximal end 472 of the engagement mechanism 464 by the distance $d_2$ illustrated in FIG. 14 when the delivery device 100 is at rest (i.e., outside a patient's body and prior to being used in a delivery procedure). In particular, the distance $d_2$ is selected to be greater than the maximum elongation the flexible inner shaft 136/flexible outer shaft 140 assembly is expected to experience during delivery of the implant 128 under normal operating conditions, with additional margin for safety. For example, where the distance between the proximal and distal ends 108, 112 (see FIG. 1) of the delivery pusher 104 is approximately 185 cm, the distance $d_2$ is typically chosen to be between about 0.03" and about 0.04" (i.e., about 0.76 mm and about 1.02 mm). As one of ordinary skill in the art will understand, however, this distance $d_2$ may be increased or decreased when a delivery pusher 104 of a different length is employed, when different materials with different material properties and associated elongation characteristics are used in the construction of the delivery device 100, when (depending on the application) a greater amount of friction is expected to be encountered during delivery of the implant 128, or for other reasons.

Referring again to FIG. 14, with the distance $d_2$ so chosen, the operator must retract (e.g., pull) the handle slider 404 in the direction of arrow 492 by a distance equal to the difference between the distance $d_2$ and the amount of elongation present in the flexible inner shaft 136/flexible outer shaft 140 assembly in order to abut the proximal end 472 of the engagement mechanism 464 and the engagement member 488 at the proximal end 484 of the first elongate member 144 and in order to initiate mechanical release of the implant 128 from the distal end 112 of the delivery pusher 104. In particular, once the proximal end 472 of the engagement mechanism 464 abuts the engagement member 488 at the proximal end 484 of the first elongate member 144, further retraction of the handle slider 404 by the operator with sufficient force will cause the distal end of the first elongate member 144 to dislodge from the distal edge of the notch 192 or from between the displacing element 156 and the inner surface of the delivery pusher 104 and will cause the first elongate member 144 to begin retracting in the direction of arrow 492. Then, by continuing to retract the first elongate member 144 in the direction of arrow 492, the operator will cause the previously-described sequence of steps depicted in FIGS. 4A-4F and 5A-5F to take place, which eventually results in the release of the implant 128 from the distal end 112 of the delivery pusher 104. Movement of the handle slider 404 may be accomplished by any of a variety of techniques, including by sliding with thumb or finger pressure, by pulling or pushing a protrusion or finger loop, by squeezing or rotating a pivoting lever, by turning a knob, etc.

In operation, the implant 128 may be introduced, delivered, positioned, and implanted at the desired site within the patient's vasculature using a micro-catheter. In particular, in treating neurovascular or peripheral vascular conditions requiring embolization, the sites may be first accessed by the micro-catheter, which is a flexible, small diameter catheter (typically with an inside diameter between 0.016" to 0.021"), through an introducer sheath/guiding catheter combination that is placed in the femoral artery or groin area of the patient. The micro-catheter may be guided to the site through the use of guidewires. Guidewires are typically long, torqueable proximal wire sections with more flexible distal wire sections designed to be advanced within tortuous vessels. A guidewire is visible using fluoroscopy and is typically used to first access the desired site, thereby allowing the micro-catheter to be reliably advanced over the guidewire to the target site.

In one embodiment, once the target site has been accessed with the micro-catheter tip, the catheter lumen is cleared by removing the guidewire, and the locked implant 128 is placed into the proximal open end of the micro-catheter and advanced by its delivery pusher 104 through the micro-catheter. When the implant 128 reaches the distal end of the micro-catheter, it is deployed from the micro-catheter and positioned by the delivery pusher 104 into the target vascular site. The operator (e.g., a physician) may advance and retract the implant 128 several times to obtain a desirable position of the implant 128 within the lesion. Once the implant 128 is satisfactorily positioned within the lesion, the detachment handle 118 is actuated to mechanically release the implant 128 into the lesion, as described above. Then, once detachment of the implant 128 has been confirmed, the delivery pusher 104 is removed from the micro-catheter, and additional implants 128 may be placed in the same manner, as necessary for proper treatment.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A device for delivering an implant to a vascular disorder of a patient, comprising:
    a delivery pusher comprising a proximal end and a distal end and defining a lumen between the proximal and distal ends;
    a moveable element defining a passageway therethrough and disposed within the lumen; and
    first and second elongate members disposed within the lumen, at least a portion of each of the first and second elongate members passing through the passageway and a first bumper element coupled to the second elongate member such that movement of the first elongate member in a first direction causes a time-delayed movement of the second elongate member in the first direction.

2. The device of claim 1, wherein the moveable element is selected from the group consisting of a floating tube and a floating coil.

3. The device of claim 1, wherein at least one of the first and second elongate members comprises a core wire.

4. The device of claim 1, wherein the first elongate member is configured to lock the implant to prevent release of the implant from the delivery pusher.

5. The device of claim 4, wherein the movement of the first elongate member in the first direction unlocks the implant, thereby permitting release of the implant from the delivery pusher.

6. The device of claim 1, wherein the movement of the first elongate member in the first direction further causes a movement of the moveable element in the first direction.

7. The device of claim 1 further comprising a second bumper element coupled to the first elongate member.

8. The device of claim 7, wherein the second bumper element is adapted to move the moveable element in the first direction when the first elongate member is moved in the first direction.

9. The device of claim 7, wherein the second bumper element is selected from the group consisting of a tube and a coil.

10. The device of claim 1, wherein the moveable element is adapted to move the first bumper element in the first direction when the first elongate member is moved in the first direction.

11. The device of claim 1, wherein the first bumper element is selected from the group consisting of a tube and a coil.

12. The device of claim 1 further comprising an element for displacing the implant from the delivery pusher.

13. The device of claim 12, wherein the displacing element is coupled to a distal end of the second elongate member.

14. The device of claim 12, wherein the displacing element comprises a tapered surface.

15. A method for delivering an implant to a vascular disorder of a patient, comprising the steps of:
advancing the implant, via a delivery pusher comprising a proximal end and a distal end and defining a lumen between the proximal and distal ends, in proximity to the vascular disorder; and
moving a first elongate member in a first direction within the lumen of the delivery pusher, wherein at least a portion of each of the first elongate member and a second elongate member pass through a passageway of a moveable element disposed within the lumen of the delivery pusher and a first bumper element is coupled to the second elongate member, and further wherein the movement of the first elongate member in the first direction causes a time-delayed movement of the second elongate member in the first direction within the lumen of the delivery pusher so as to release the implant from the delivery pusher.

16. The method of claim 15, wherein the moveable element is selected from the group consisting of a floating tube and a floating coil.

17. The method of claim 15, wherein at least one of the first and second elongate members comprises a core wire.

18. The method of claim 15, wherein the implant is locked to the delivery pusher prior to the step of moving the first elongate member in the first direction.

19. The method of claim 18, wherein moving the first elongate member in the first direction unlocks the implant, thereby permitting release of the implant from the delivery pusher.

20. The method of claim 15, wherein moving the first elongate member in the first direction moves the moveable element in the first direction.

21. The method of claim 20, wherein movement of the moveable element in the first direction moves the second elongate member in the first direction.

22. The method of claim 15, wherein the implant comprises an embolic coil.

23. The method of claim 22, wherein the implant further comprises at least one of a proximal tab and a suture loop adapted to couple a proximal end of the embolic coil to the distal end of the delivery pusher.

* * * * *